Figure 1:
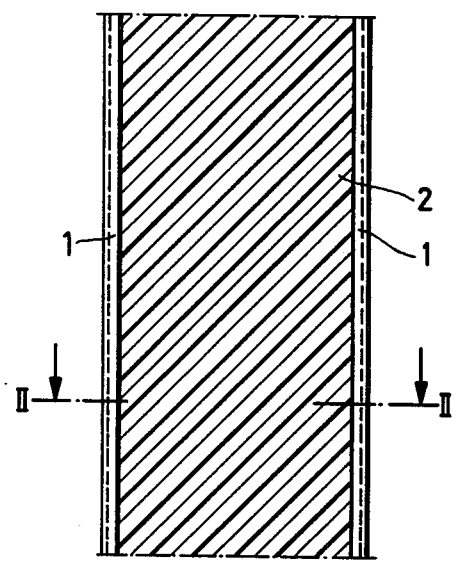

United States Patent [19]

Krick

[11] 4,362,163
[45] Dec. 7, 1982

[54] STIFFENING CORE FOR CATHETERS

[75] Inventor: Gerd Krick, Bad Homburg, Fed. Rep. of Germany

[73] Assignee: Eduard Fresenius Chem.-Pharm. Industrie KG Apparatebau KG, Fed. Rep. of Germany

[21] Appl. No.: 212,090

[22] PCT Filed: Mar. 28, 1979

[86] PCT No.: PCT/DE79/00032
§ 371 Date: Nov. 28, 1979
§ 102(e) Date: Nov. 28, 1979

[30] Foreign Application Priority Data

Mar. 28, 1978 [DE] Fed. Rep. of Germany ....... 2813276

[51] Int. Cl.³ .............................................. A61M 25/00
[52] U.S. Cl. .................................... 604/280; 128/341
[58] Field of Search ................................ 128/348–350, 128/341, 303 R, 657, 658, 772, DIG. 9

[56] References Cited

U.S. PATENT DOCUMENTS

| 3,169,528 | 2/1965 | Knox et al. | 128/350 R |
| 3,419,010 | 12/1968 | Williamson | 128/350 R |
| 3,731,671 | 5/1973 | Mageoh | 128/772 |
| 3,777,761 | 12/1973 | Sheridan | 128/350 R |
| 3,973,556 | 8/1976 | Fleischhacker | 128/772 |
| 4,257,421 | 3/1981 | Beal | 128/348 |

FOREIGN PATENT DOCUMENTS 2017182 10/1979 United Kingdom ................ 128/772

Primary Examiner—Dalton L. Truluck
Attorney, Agent, or Firm—Perry Carvellas

[57] ABSTRACT

In a stiffening core for catheters, a plurality of spaced apart wires, which are circular in cross-section are inserted in the surface of a continuous strip of soft plastic material and are embedded by said strip to more than one-half of their cross-sections. Owing to this design, the stiffening core has a stiffness, flexibility and elasticity which can be reproduced within close limits.

14 Claims, 3 Drawing Figures

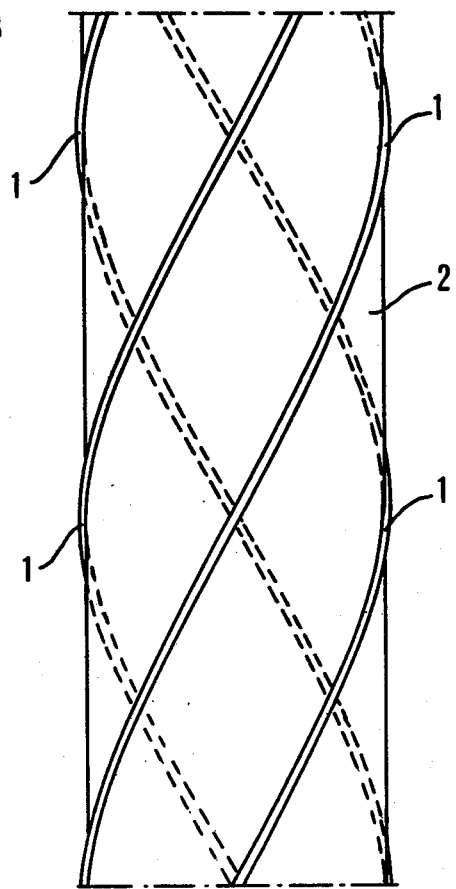

STIFFENING CORE FOR CATHETERS

This invention relates to a stiffening core for catheters, which consists of a circular-section continuous strip of plastic material which is provided with a wire insert.

U.S. Pat. No. 3,973,556 discloses a stiffening core which consists of a coil spring surrounding an inner wire. The convolutions of said core may partly be ground on the outside or be coated with plastic material. That known stiffening core for catheter is heavy and owing to its complicated structure is expensive.

Another known stiffening core, e.g., for vein catheters, consist of an elongated strip of plastic material, which is provided with an X-ray contrast strip.

In another known stiffening core of the kind described first hereinbefore, continuous strip of plastic material contains a wire. To manufacture that stiffening core, the plastic material is extruded around the wire. The flexibility of that known stiffening core depends mainly on the nature of the plastic material. It is known that the flexibility and elasticity of the plastic material vary within relatively large tolerance ranges.

For this reason it is an object of the present invention to provide a stiffening core which as regards stiffness, flexibility and elasticity has properties which are reproducible within close limits.

This object is accomplished according to the invention in that a plurality of spaced-apart circular-section wires are inserted in the surface of a continuous strip of soft plastic material and are contacted by the plastic material around more than one-half of their cross-section. In the stiffening core according to the invention, a very soft plastic material is used, which serves substantially only as a filling material whereas the stiffness, flexibility and restoring force of the stiffening core are mainly determined by the metal wire. As a result, the flexibility and elasticity of the stiffening core depend no longer on the properties of the plastic material which is used, which properties can be reproduced only with difficulty from batch to batch with the accuracy which is required. Because the required flexibility and elasticity of the stiffening core are ensured by the wires, a very soft plastic material may be used and its hardness need not be controlled within close limits. As a result, the stiffening core according to the invention distinguishes by a more uniform elasticity and flexibility and for this reason can better meet the requirements encountered in practice.

Besides, the stiffening core according to the invention can be more easily shifted in the flexible catheter tube because those wire portions which protrude from the surface of the continuous elongated body of plastic material are approximately crescent-shaped in cross-section and bear on the inside surface of the catheter and act as guides. As the stiffening core and catheter are in almost linear contact, the friction between them is decreased. This is particularly important because the catheter which has been placed will not be displaced as the stiffening core is extracted. The wires provided on the surface of the stiffening core impart a high elasticity to said core so that the latter when deflected by an obstacle will tend to return to its original position owing to its restoring force. For this reason, catheters can be placed more easily with the aid of the stiffening core according to the invention.

The wires may extend axially of the plastic strip or may helically embrace it. If the wires extend helically on the surface of the plastic strip, the stiffening core and the catheter will be able to follow very easily the curvatures and radii of the path along which they are to be placed.

Preferred further features of the invention will be described more fully in the sub-claims.

Figure 2:
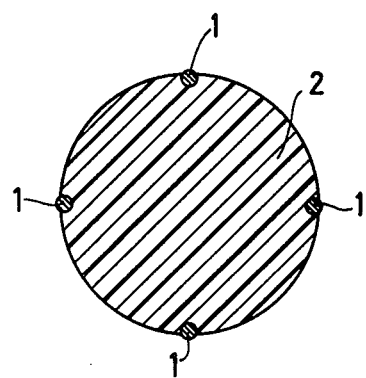

An embodiment of the invention will be explained more in detail and by way of example with reference to the drawing, in which FIG. 1 is a longitudinal sectional view showing a portion of a stiffening core and FIG. 2 is a transverse sectional view showing the stiffening core of FIG. 1.

FIG. 3 is an elevational side view showing the wires extending helically along the surface of the core material.

The stiffening core comprises a circular-section strip 2 of a soft plastic material and four axial wires 1, which are provided on the surface of the strip 2 and regularly spaced apart. The wires 1 are received in the surface of the plastic strip 2 to such an extent that only one-third of the cross-section of each wire protrudes from the strip 2. As a result, the wires are reliably held in the plastic strip.

Referring to FIG. 1 and FIG. 2 of the drawings, there is illustrated a stiffening core for catheters having a circular cross-section continuous plastic strip core material 2. The core material 2 has inserted on the outer surface thereof a plurality of, e.g. four, wire inserts 1. The wire inserts 1 have a uniform shape cross-section and are axially disposed along and evenly spaced around the outer surface of the stiffening core material 2. The wire inserts 1 are inserted in the outer surface of the core material 2 to a depth of at least more than one half of the cross-section of said wire inserts 1.

Referring to FIG. 3 of the drawings, there is illustrated a stiffening core for catheters having a circular cross-section continuous plastic strip core material 2. The core material 2 has inserted on the outer surface thereof a plurality of, e.g. four, wire inserts 1. The wire inserts 1 have a uniform shape cross-section and are equally spaced apart and extend helically along the length and outer surface of the stiffening core material 2. The wire inserts 1 are inserted in the outer surface of the continuous core material 2 to a depth of at least more than one half of the cross-section of said wire inserts 1.

The wires are very thin relative to the cross-section of the plastic strip and are dimensioned to impart the required flexibility and elasticity to the stiffening core.

The wires consist preferably of stainless steel.

To manufacture the stiffening core, the wires are extruded with the plastic strip or are forced into the strip immediately after it has been extruded.

I claim:

1. A stiffening core for catheters comprising a circular-section continuous strip of soft plastic core material which is provided with a plurality of evenly spaced-apart circular-section wire inserts in the outer surface of said continuous strip plastic core material and which are inserted in the outer surface of said plastic material to a depth of more than one-half of the cross-section of the wire insert.

2. The stiffening core material of claim 1, wherein the wires extend axially along the length of the plastic core material.

3. The stiffening core material of claim 1, wherein the wires extend helically along the length of the plastic core material.

4. The stiffening core material of claim 1 wherein two wires are provided on the outer surface of the plastic core material to stiffen the same.

5. The stiffening core material of claim 1 wherein there are three or four wires that are evenly spaced apart.

6. The stiffening core material of claim 1 wherein the wire inserts are inserted into the outer surface of the core material to a depth of about two-thirds of the cross-sections of the wires.

7. A stiffening core for catheters comprising a circular cross-section continuous plastic strip core material, said core material having inserted on the outer surface thereof a plurality of wire inserts, said wire inserts having a uniform shape cross-section and being axially disposed along and evenly spaced around the outer surface of said stiffening core material, and said wire inserts being inserted in the outer surface of said continuous core material to a depth of at least more than one half of the cross-section of said wire inserts.

8. The stiffening core material of claim 7 wherein there are three to four wire inserts.

9. The stiffening core material of claim 7 wherein the wires are circular in cross-section and are inserted to a depth of about two-thirds of the wire cross-section.

10. The stiffening core material of claim 7 wherein said core material consists of soft plastic.

11. A stiffening core for catheters comprising a circular cross-section continuous plastic strip core material, said core material having inserted on the outer surface thereof a plurality of wire inserts, said wire inserts having a uniform shape cross-section, and being equally spaced apart and extending helically along the length and outer surface of said stiffening core material, and said wire inserts being inserted in the outer surface of said continuous core material to a depth of at least more than one half of the cross-section of said wire inserts.

12. The stiffening core material of claim 11 wherein there are three to four wire inserts.

13. The stiffening core material of claim 11 wherein the wires are circular in cross-section and are inserted to a depth of about two-thirds of the wire cross-section.

14. The stiffening core material of claim 11 wherein said core material consists of soft plastic.

* * * * *